US 6,702,832 B2

(12) United States Patent
Ross et al.

(10) Patent No.: US 6,702,832 B2
(45) Date of Patent: Mar. 9, 2004

(54) MEDICAL DEVICE FOR CUTTING A CORNEA THAT HAS A VACUUM RING WITH A SLITTED VACUUM OPENING

(75) Inventors: Rod Ross, Laguna Niguel, CA (US); Greggory Hughes, Fountain Valley, CA (US)

(73) Assignee: Med Logics, Inc., Laguna Hills, CA (US)

( * ) Notice: Subject to any disclaimer, the term of this patent is extended or adjusted under 35 U.S.C. 154(b) by 0 days.

(21) Appl. No.: 10/272,567

(22) Filed: Oct. 15, 2002

(65) Prior Publication Data
US 2003/0045895 A1 Mar. 6, 2003

Related U.S. Application Data

(62) Division of application No. 09/349,835, filed on Jul. 8, 1999.

(51) Int. Cl.[7] .................................................. A61F 9/00
(52) U.S. Cl. ........................................................ 606/166
(58) Field of Search ............................. 606/4, 5, 6, 166, 606/167, 169, 172

(56) References Cited

U.S. PATENT DOCUMENTS

| 1,841,968 A | 1/1932 | Lowry |
| 1,847,658 A | 3/1932 | Lasker |
| 2,070,281 A | 2/1937 | Leggiadro |
| 2,480,737 A | 8/1949 | Jayle |
| RE23,496 E | 5/1952 | Seeler |
| 2,708,437 A | 5/1955 | Hutchins |
| 2,824,455 A | 2/1958 | Ristow et al. |
| 3,033,196 A | 5/1962 | Hay |
| 3,252,623 A | 5/1966 | Corbin et al. |
| 3,266,494 A | 8/1966 | Brownrigg et al. |
| 3,308,828 A | 3/1967 | Pippin |
| 3,399,677 A | 9/1968 | Gould et al. |
| 3,511,162 A | 5/1970 | Truhan |
| 3,561,429 A | 2/1971 | Jewett |

(List continued on next page.)

FOREIGN PATENT DOCUMENTS

| DE | 25 47 185 | 4/1977 |
| EP | 1033 120 A2 | 6/2000 |
| FR | 2 549 727 | 7/1963 |

OTHER PUBLICATIONS

Steinway Instrument Company Inc., The Steinway/Barraquer in–Situ Microkeratome Set.

(List continued on next page.)

Primary Examiner—Michael J. Milano
Assistant Examiner—Victor Nguyen
(74) Attorney, Agent, or Firm—Irell & Manella LLP

(57) ABSTRACT

A medical device that can be used to cut a cornea. The device may include a blade that is coupled to a head by a blade holder. The device may also have a retention spring that exerts a force on the blade and blade holder. The head and blade can be moved across a ring by a drive assembly that contains a lead screw. The ring may contain one or more openings which have a length that is greater than a width. The openings may be coupled to a vacuum source by a tube. The vacuum pressure of the tube can be displayed by a console. The console may also have switches that allow different operating parameters to be entered through a single knob.

8 Claims, 12 Drawing Sheets

U.S. PATENT DOCUMENTS

| | | | |
|---|---|---|---|
| 3,583,403 | A | 6/1971 | Pohl |
| 3,589,363 | A | 6/1971 | Banko |
| 3,624,821 | A | 11/1971 | Henderson |
| 3,693,613 | A | 9/1972 | Kelman |
| 3,723,030 | A | 3/1973 | Gelfand |
| 3,752,161 | A | 8/1973 | Bent |
| 3,763,862 | A | 10/1973 | Spieth |
| 3,812,855 | A | 5/1974 | Banko |
| 3,815,604 | A | 6/1974 | O'Malley et al. |
| 3,841,799 | A | 10/1974 | Spinosa et al. |
| 3,842,839 | A | 10/1974 | Malis et al. |
| 3,882,872 | A | 5/1975 | Douvas et al. |
| 3,884,238 | A | 5/1975 | O'Malley et al. |
| 3,899,829 | A | 8/1975 | Storm et al. |
| 3,903,881 | A | 9/1975 | Weigl |
| 3,913,584 | A | 10/1975 | Walchle et al. |
| 3,920,014 | A | 11/1975 | Banko |
| 3,930,505 | A | 1/1976 | Wallach |
| 3,945,117 | A | 3/1976 | Beaver |
| 3,977,425 | A | 8/1976 | Hayashida |
| 3,982,539 | A | 9/1976 | Muriot |
| 3,983,474 | A | 9/1976 | Kuipers |
| 3,986,512 | A | 10/1976 | Walliser |
| 4,004,590 | A | 1/1977 | Muriot |
| 4,011,869 | A | 3/1977 | Seiler, Jr. |
| 4,034,712 | A | 7/1977 | Duncan |
| 4,043,342 | A | 8/1977 | Morrison, Jr. |
| 4,108,182 | A | 8/1978 | Hartman et al. |
| 4,135,515 | A | 1/1979 | Muriot |
| 4,137,920 | A | 2/1979 | Bonnet |
| 4,168,707 | A | 9/1979 | Douvas et al. |
| 4,173,980 | A | 11/1979 | Curtin |
| 4,178,707 | A | 12/1979 | Littlefield |
| 4,204,328 | A | 5/1980 | Kutner |
| 4,205,682 | A | 6/1980 | Crock et al. |
| 4,210,146 | A | 7/1980 | Banko |
| 4,217,993 | A | 8/1980 | Jess et al. |
| 4,223,676 | A | 9/1980 | Wuchinich et al. |
| 4,245,815 | A | 1/1981 | Willis |
| 4,246,902 | A | 1/1981 | Martinez |
| 4,274,411 | A | 6/1981 | Dotson, Jr. |
| 4,301,802 | A | 11/1981 | Poler |
| 4,304,262 | A | 12/1981 | Icking |
| 4,308,385 | A | 12/1981 | Goorden |
| 4,308,835 | A | 1/1982 | Abbey |
| 4,314,560 | A | 2/1982 | Helfgott et al. |
| 4,319,899 | A | 3/1982 | Marsh |
| 4,320,761 | A | 3/1982 | Haddad |
| 4,344,784 | A | 8/1982 | Deckas et al. |
| 4,354,838 | A | 10/1982 | Hoyer et al. |
| 4,395,258 | A | 7/1983 | Wang et al. |
| 4,396,386 | A | 8/1983 | Kurtz et al. |
| 4,427,427 | A | 1/1984 | DeVecchi |
| 4,428,748 | A | 1/1984 | Peyman et al. |
| 4,429,696 | A | 2/1984 | Hanna |
| 4,445,517 | A | 5/1984 | Feild |
| 4,474,411 | A | 10/1984 | Peters et al. |
| 4,475,904 | A | 10/1984 | Wang |
| 4,476,862 | A | 10/1984 | Pao |
| 4,479,717 | A | 10/1984 | Cornillault |
| 4,481,948 | A | 11/1984 | Sole |
| 4,493,695 | A | 1/1985 | Cook |
| 4,493,698 | A | 1/1985 | Wang et al. |
| 4,522,371 | A | 6/1985 | Fox et al. |
| 4,523,911 | A | 6/1985 | Braetsch et al. |
| 4,524,948 | A | 6/1985 | Hall |
| 4,530,357 | A | 7/1985 | Pawloski et al. |
| 4,531,934 | A | 7/1985 | Kossovsky et al. |
| 4,540,406 | A | 9/1985 | Miles |
| 4,555,645 | A | 11/1985 | Atkinson |
| 4,560,395 | A | 12/1985 | Davis |
| 4,583,539 | A | * 4/1986 | Karlin et al. ............... 606/4 |
| 4,589,414 | A | 5/1986 | Yoshida et al. |
| 4,598,729 | A | 7/1986 | Naito et al. |
| 4,647,209 | A | 3/1987 | Neukomm et al. |
| 4,660,556 | A | 4/1987 | Swinger et al. |
| 4,660,970 | A | 4/1987 | Ferrano |
| 4,662,370 | A | 5/1987 | Hoffmann et al. |
| 4,665,914 | A | 5/1987 | Tanne |
| 4,674,499 | A | 6/1987 | Pao |
| 4,674,503 | A | 6/1987 | Peyman et al. |
| 4,678,459 | A | 7/1987 | Onik et al. |
| 4,688,570 | A | 8/1987 | Kramer et al. |
| 4,690,099 | A | 9/1987 | Gregan et al. |
| 4,701,049 | A | 10/1987 | Beckmann et al. |
| 4,705,395 | A | 11/1987 | Hageniers |
| 4,706,687 | A | 11/1987 | Rogers |
| 4,723,545 | A | 2/1988 | Nixon et al. |
| 4,743,770 | A | 5/1988 | Lee |
| 4,757,814 | A | 7/1988 | Wang et al. |
| 4,759,363 | A | 7/1988 | Jensen |
| 4,767,403 | A | 8/1988 | Hodge |
| 4,768,506 | A | 9/1988 | Parker et al. |
| 4,770,654 | A | 9/1988 | Rogers et al. |
| 4,782,239 | A | 11/1988 | Hirose et al. |
| 4,782,849 | A | 11/1988 | Hodge |
| 4,791,934 | A | 12/1988 | Brunnett |
| 4,805,615 | A | 2/1989 | Carol |
| 4,805,616 | A | 2/1989 | Pao |
| 4,807,623 | A | 2/1989 | Lieberman |
| 4,819,635 | A | 4/1989 | Shapiro |
| 4,825,091 | A | 4/1989 | Breyer et al. |
| 4,828,306 | A | 5/1989 | Blatt |
| 4,830,047 | A | 5/1989 | Hodge |
| 4,837,857 | A | 6/1989 | Scheller et al. |
| 4,838,281 | A | 6/1989 | Rogers et al. |
| 4,840,175 | A | 6/1989 | Peyman |
| 4,865,033 | A | 9/1989 | Krumeich et al. |
| 4,884,570 | A | 12/1989 | Krumeich et al. |
| 4,886,085 | A | 12/1989 | Miller |
| 4,903,695 | A | 2/1990 | Warner et al. |
| 4,909,815 | A | 3/1990 | Meyer |
| RE33,250 | E | 7/1990 | Cook |
| 4,941,093 | A | * 7/1990 | Marshall et al. ............... 606/5 |
| 4,943,289 | A | 7/1990 | Goode et al. |
| 4,965,417 | A | 10/1990 | Massie |
| 4,988,347 | A | 1/1991 | Goode et al. |
| 4,997,437 | A | 3/1991 | Grieshaber |
| 5,011,482 | A | 4/1991 | Goode et al. |
| 5,013,310 | A | 5/1991 | Goode et al. |
| 5,019,076 | A | 5/1991 | Yamanashi et al. |
| 5,059,204 | A | 10/1991 | Lawson et al. |
| 5,083,558 | A | 1/1992 | Thomas et al. |
| 5,098,443 | A | 3/1992 | Parel et al. |
| 5,106,364 | A | 4/1992 | Hayafuji et al. |
| 5,133,713 | A | 7/1992 | Huang et al. |
| 5,133,726 | A | 7/1992 | Ruiz et al. |
| 5,152,786 | A | * 10/1992 | Hanna ............... 623/5.11 |
| 5,176,628 | A | 1/1993 | Charles et al. |
| 5,201,749 | A | 4/1993 | Sachse et al. |
| 5,207,683 | A | 5/1993 | Goode et al. |
| 5,215,104 | A | 6/1993 | Steinert |
| 5,217,459 | A | 6/1993 | Kamerling |
| 5,224,950 | A | 7/1993 | Prywes |
| 5,226,910 | A | 7/1993 | Kajiyama et al. |
| 5,242,404 | A | 9/1993 | Conley et al. |
| 5,271,379 | A | 12/1993 | Phan et al. |
| 5,273,406 | A | 12/1993 | Feygin |
| 5,273,524 | A | 12/1993 | Fox et al. |
| 5,285,795 | A | 2/1994 | Ryan et al. |
| 5,322,505 | A | 6/1994 | Krause et al. |

| | | |
|---|---|---|
| 5,330,470 A | 7/1994 | Hagen |
| 5,354,268 A | 10/1994 | Peterson et al. |
| 5,364,395 A | 11/1994 | West, Jr. |
| 5,374,188 A | 12/1994 | Frank et al. |
| 5,380,280 A | 1/1995 | Peterson |
| 5,383,454 A | 1/1995 | Bucholz |
| 5,395,368 A | 3/1995 | Ellman et al. |
| 5,403,276 A | 4/1995 | Schechter et al. |
| 5,403,311 A | 4/1995 | Abele et al. |
| 5,437,678 A | 8/1995 | Sorensen |
| 5,465,633 A | 11/1995 | Bernloehr |
| 5,474,532 A | 12/1995 | Steppe |
| 5,476,448 A | 12/1995 | Urich |
| 5,476,473 A | 12/1995 | Heckele |
| 5,496,339 A | 3/1996 | Koepnick |
| 5,507,751 A | 4/1996 | Goode et al. |
| 5,520,684 A | 5/1996 | Imran |
| 5,527,332 A | 6/1996 | Clement |
| 5,527,356 A | 6/1996 | Peyman et al. |
| 5,531,744 A | 7/1996 | Nardella et al. |
| 5,556,397 A | 9/1996 | Long et al. |
| 5,566,681 A | 10/1996 | Manwaring et al. |
| RE35,421 E | 1/1997 | Ruiz et al. |
| D377,524 S | 1/1997 | Lipp |
| 5,611,799 A | 3/1997 | Smith |
| 5,624,394 A | 4/1997 | Barnitz et al. |
| 5,643,304 A | 7/1997 | Schechter et al. |
| 5,651,782 A | 7/1997 | Simon et al. |
| 5,690,658 A | 11/1997 | McAdams |
| 5,693,013 A | 12/1997 | Geuder |
| 5,700,240 A | 12/1997 | Barwick, Jr. et al. |
| 5,704,927 A | 1/1998 | Gillette et al. |
| 5,738,677 A | 4/1998 | Colvard et al. |
| 5,743,274 A | 4/1998 | Peyman |
| 5,755,700 A | 5/1998 | Kritzinger et al. |
| 5,779,723 A | 7/1998 | Schwind |
| 5,782,849 A | 7/1998 | Miller |
| 5,787,760 A | 8/1998 | Thorlakson |
| 5,795,328 A | 8/1998 | Barnitz et al. |
| 5,810,857 A | 9/1998 | Mackool |
| 5,814,010 A | 9/1998 | Ziegler |
| 5,817,075 A | 10/1998 | Giungo |
| 5,819,628 A | 10/1998 | Cogan et al. |
| 5,868,728 A | 2/1999 | Giungo et al. |
| 5,916,330 A | 6/1999 | Jacobson |
| 5,919,185 A * | 7/1999 | Peyman .................... 623/5.11 |
| 5,934,285 A | 8/1999 | Kritzinger et al. |
| 5,938,676 A | 8/1999 | Cohn et al. |
| 5,941,250 A | 8/1999 | Aramant et al. |
| 5,944,731 A | 8/1999 | Hanna |
| 5,957,921 A | 9/1999 | Mirhashemi et al. |
| 5,984,913 A | 11/1999 | Kritzinger et al. |
| 5,989,272 A | 11/1999 | Barron et al. |
| 6,004,313 A | 12/1999 | Shimmick et al. |
| 6,013,049 A | 1/2000 | Rockley et al. |
| 6,019,754 A | 2/2000 | Kawesch |
| 6,045,563 A | 4/2000 | Duprat |
| 6,051,009 A * | 4/2000 | Hellenkamp et al. ....... 606/166 |
| 6,059,805 A | 5/2000 | Sugimura et al. |
| 6,083,236 A | 7/2000 | Feingold |
| 6,086,544 A | 7/2000 | Hibner et al. |
| 6,165,189 A | 12/2000 | Ziemer |
| 6,217,594 B1 | 4/2001 | Hallen et al. |
| 6,221,067 B1 * | 4/2001 | Peyman .................... 606/5 |
| 6,251,101 B1 | 6/2001 | Glockler |
| 6,258,082 B1 | 7/2001 | Lin |
| 6,280,470 B1 * | 8/2001 | Peyman .................... 623/5.13 |
| 6,312,403 B1 | 11/2001 | Ruiz |
| 6,406,473 B1 | 6/2002 | Shimmick et al. |

OTHER PUBLICATIONS

Brochure, Site TXR Systems, Site Mycrosurgical Systems, Inc., Horsham, Pennsylvania.

Marshall M. Parks, "Intracapsular Aspiration" article, pp. 59–74.

Van Oldenborgh, "Correction of late operative complications by means of a suction cutter", Opthal. Soc. U.K. (1980), 100, 219, pp. 219–221.

Helfgott, M.D. "A System for Variable Aspiration of Material Dissected from the Posterior Chamber", Ophthalmic Surgery, vol. 15, Jun. 1984, pp. 529–350.

Coopervision Brochure on Cavitron/Kelman Model 6500 E.I.S. and Model 7500, 6 pages.

Surgical Design Brochure on "The Ocusystem", 1 page.

Coopervision Brochure on "Cavitorn/Kelman Phaco–Emulsifier Aspirator Model 8001", 2 pages.

Coopervision Brochure on Cavitron/Kelman Phaco–Emulsifier Aspirator Model 9001, 6 pages.

Greishaber of Switzerland Brochure on "MPC, The Membrane Peeler Cutter", 5 pages.

Micro–Vit Vitrectomy System Product Brochure and Instruction Manual.

Storz Irrigation Aspiration System Product Brochure and Instruction Manual.

United Surgical Corporation Brochure on "Phacotron Plus", one page.

Surgical Design Company Brochure on Keates Ultrasonic I/E Mini Probe by A. Banko, 2 pages.

Surgical Design Corporation Brochure on U.S., Phaco System, 1 page.

Coopervision Brochure on System VI, 1 page.

Murayama et al. "A Portable Air Driving Unit for Blood Pumps", Japanese Journal of Artificial Organs, vol. 14, No. 3, pp. 1206–1209 (English Translation).

Scuderi, et al., French article entitled "La Chirurgie de la Cartaracte Congenitale", pp. 174–185. (English translation).

Hayashi et al., Japanese Experience with Ventricular Assist Devices IBEE Engineering in Medicine and Biology Magazine Mar. 1986, pp. 30–36.

Grieshaber and Co. of Switzerland, "Sutherland Rotatable Intraocular Microscissors", 2 pages.

JCERS and Tissue Removal Systems, Diskecter™ System, Rapid Tissue Removal System advertisement.

Charles and Wang, "A Linear Suction Control for the Vitreous Cutter (Ocutome)", Arch. Ophthalmol. vol. 99, Sep. 1981, p. 1631.

Crosby, "On Control of Artificial Hearts", pp. 89–114.

Mrava, Cardiac Engineering, vol. 3, pp. 31–68.

* cited by examiner

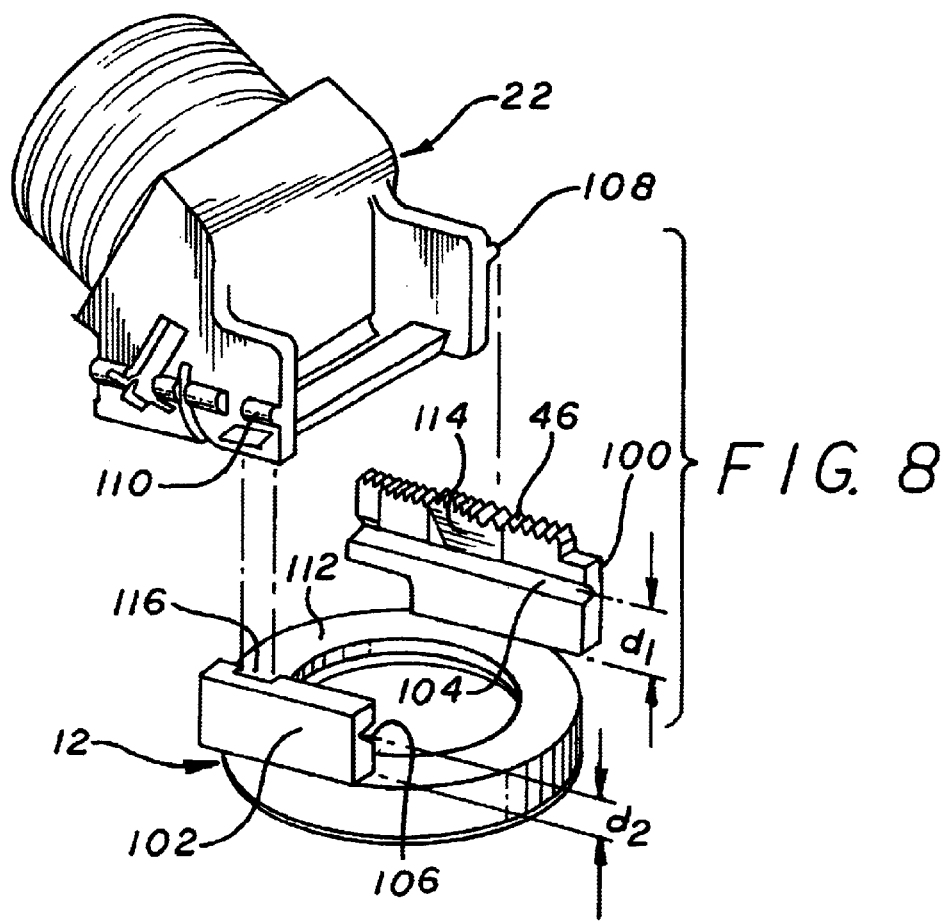
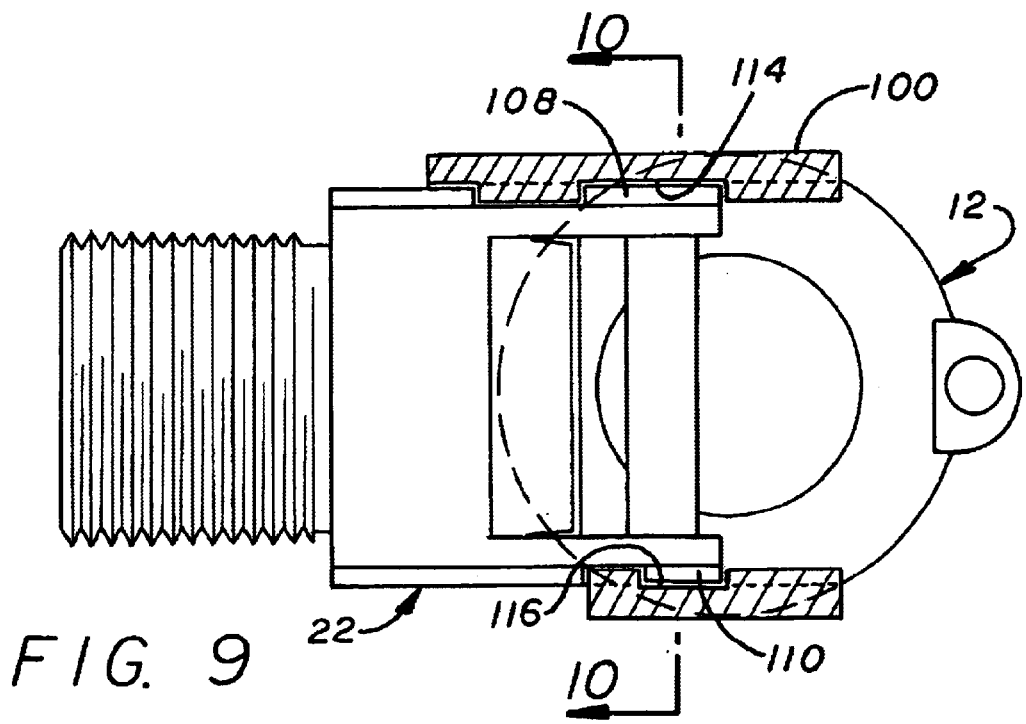

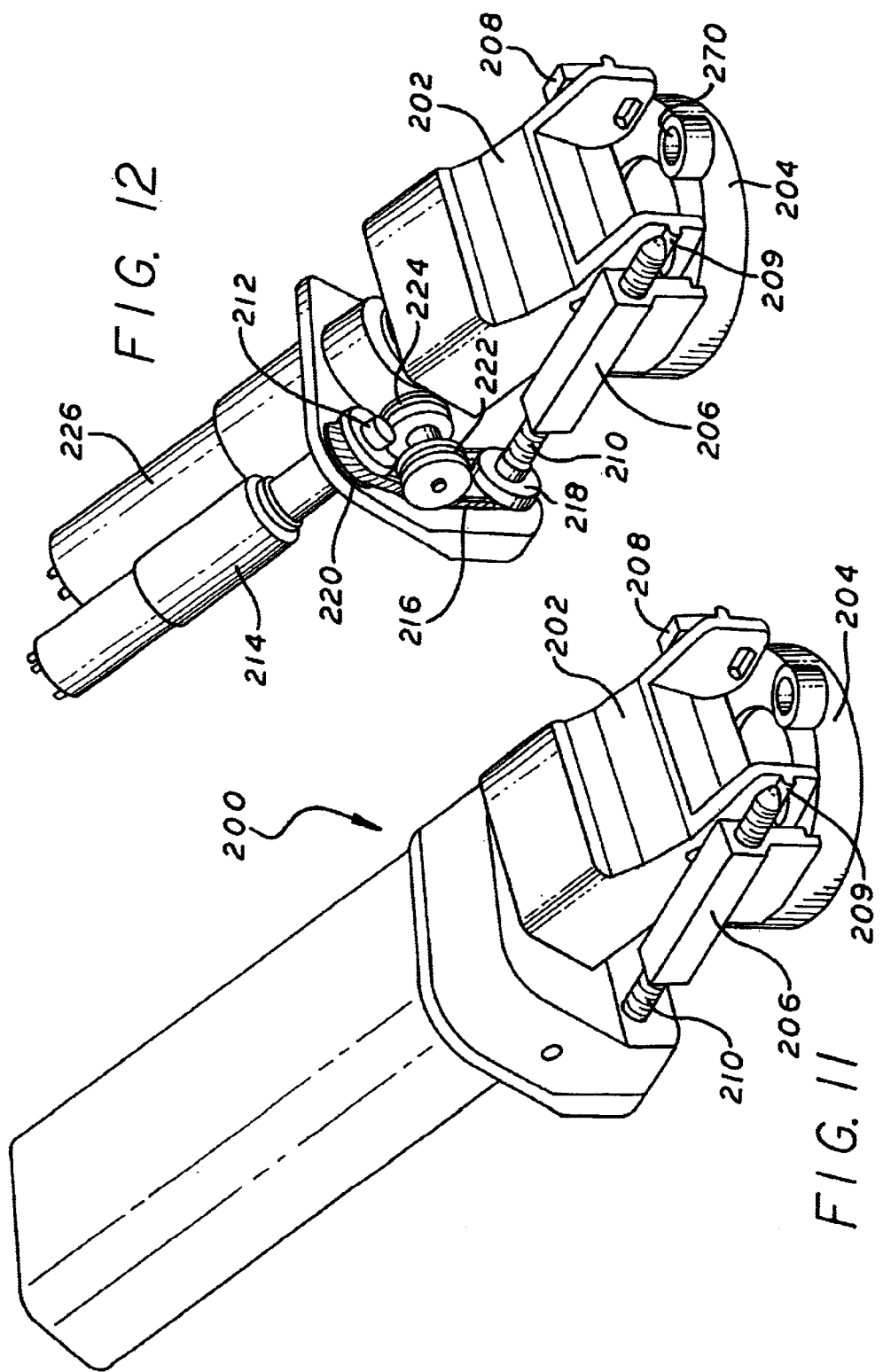

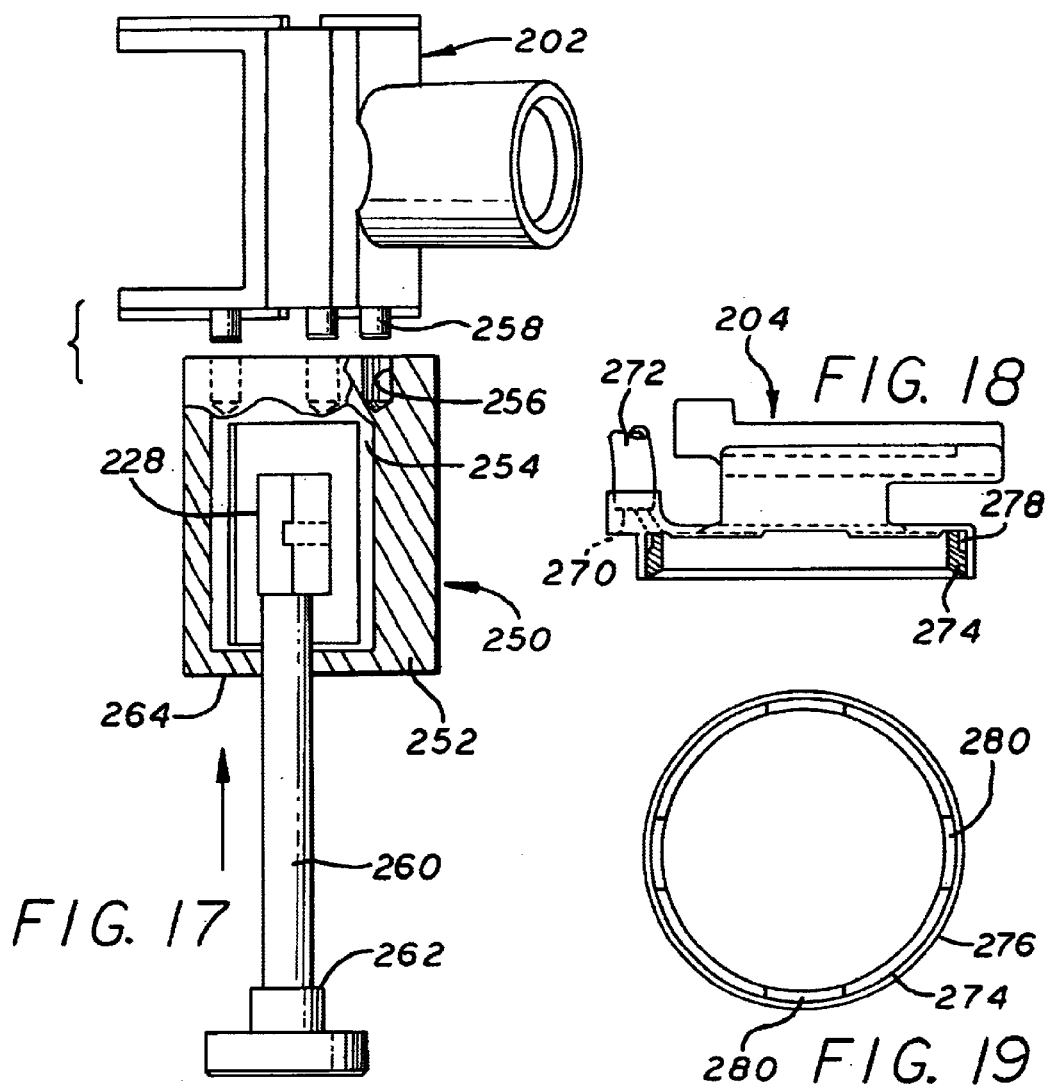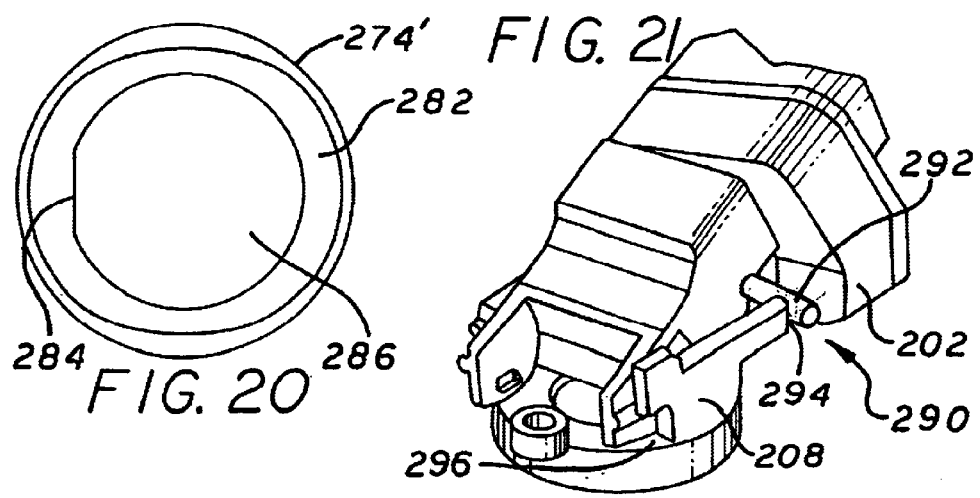

MEDICAL DEVICE FOR CUTTING A CORNEA THAT HAS A VACUUM RING WITH A SLITTED VACUUM OPENING

This application is a division of Ser. No. 09/349,835 filed Jul. 8, 1999.

BACKGROUND OF THE INVENTION

1. Field of the Invention

The present invention relates to a microkeratome that can be used to remove tissue from a cornea.

2. Background Information

There have been developed a number of different surgical techniques to correct hyperopic or myopic conditions of a human eye. U.S. Pat. No. 4,840,175 issued to Peyman discloses a procedure wherein a thin layer of corneal tissue is cut and removed from a cornea. A laser beam is then directed onto the exposed corneal tissue in a predetermined pattern. The laser beam ablates corneal tissue and changes the curvature of the eye.

U.S. Pat. No. Re. 35,421 issued to Ruiz et al. discloses a device for cutting the cornea to expose an underlying surface for laser ablation. Such a device is commonly referred to as a microkeratome. The Ruiz microkeratome includes a ring that is placed onto a cornea and a blade that is located within an opening of the ring. The device also contains a drive mechanism which moves the blade across the cornea in a first direction while sliding the blade across the eye in a second transverse direction. The device can create a lamella which is flipped back so that the eye can be ablated with the laser.

The Ruiz microkeratome includes a head that houses the blade. The drive mechanism of the keratome moves the head and the blade across the opening of the ring. The head and ring have a pair of dovetail tongue and groove linear bearings which insure that the blade moves in a linear manner across the cornea.

The dovetail configuration of the Ruiz microkeratome requires that the head be loaded from the side of the ring. The surgeon must align the dovetail features before sliding the head onto the ring. Aligning the dovetail features can be difficult and awkward. It would be desirable to provide a microkeratome that can be more readily assembled than keratomes of the prior art.

The blade is typically assembled into a blade holder that is captured by the head of the microkeratome. The surgeon assembles the blade into the blade holder and then loads the blade holder into an opening in the head. To avoid contamination the surgeon typically holds the blade with a magnet.

It is important to accurately assemble the blade into the blade holder and load the blade holder into the head. A misalignment of the blade may result in an inaccurate cut of the cornea. It would therefore be desirable to provide a microkeratome and a tool that insure an accurate loading of the blade.

Microkeratomes that are presently used in the field typically have a stop feature that limits the movement of the blade across the cornea. The stop feature may include a pin that extends from the head and engages a stop surface of the ring. It has been found that a portion of the patient's eyelid may fall in between the pin and the stop surface. The eyelid may prematurely stop the head and create an inaccurate cut of the cornea. It would be desirable to provide a stop feature that was not susceptible to interference from an object such as an eyelid.

Most conventional microkeratome drive mechanisms contain a plurality of spur gears that are coupled to a single drive motor. The gears rotate to move the blade and head across the ring to cut the cornea. Spur gears are susceptible to wear and crowning. Additionally, the vibration of the motor may transfer to the blade through the gears and affect the cutting action of the blade. It would be desirable to provide a microkeratome that was less susceptible to gear wear and crowning, and absorbed at least some of the vibration energy generated by the motor.

The vacuum ring typically has one or more openings that are in fluid communication with a source of vacuum. The vacuum holds the ring in place while the blade cuts the cornea. It has been found that the opening(s) may become occluded and prevent an adequate vacuum pressure to hold the ring in place during the procedure. Any movement of the ring during the cutting process may result in an improper cut of the cornea. Unfortunately, the surgeon has no means to determine whether there is an inadequate vacuum pressure at the ring/cornea interface. It would be desirable to provide a microkeratome that reduced the likelihood of an occlusion at the ring openings and provided an indication to the surgeon when there is inadequate vacuum pressure at the ring/cornea interface.

SUMMARY OF THE INVENTION

One embodiment of the present invention is a medical device that can be used to cut a cornea. The device may include a blade that is coupled to a head by a blade holder. The device may also have a retention spring that exerts a force on the blade and blade holder. The head and blade can be moved across a ring by a drive assembly that contains a lead screw. The ring may contain one or more openings which have a length that is greater than a width. The openings may be coupled to a vacuum source by a tube. The vacuum pressure of the tube can be displayed by a console. The console may also have switches that allow different operating parameters to be entered through a single knob.

BRIEF DESCRIPTION OF THE DRAWINGS

FIG. 8 is an exploded view of an alternate embodiment of a head and a ring;

FIG. 9 is a cross-sectional view of the head and ring;

FIG. 11 is a perspective view of an alternate embodiment of the medical device;

FIG. 12 is a perspective view showing a belt and pulley mechanism of the device;

FIG. 17 is a top sectional view of a blade loader that can be used to insert the blade holder assembly into the head;

FIG. 18 is a side sectional view of a ring of the device;

FIG. 19 is a bottom view of a ring insert;

FIG. 20 is a top sectional view showing an alternate embodiment of the ring;

FIG. 21 is a perspective view showing a stop of the device;

DETAILED DESCRIPTION

Figure 1:
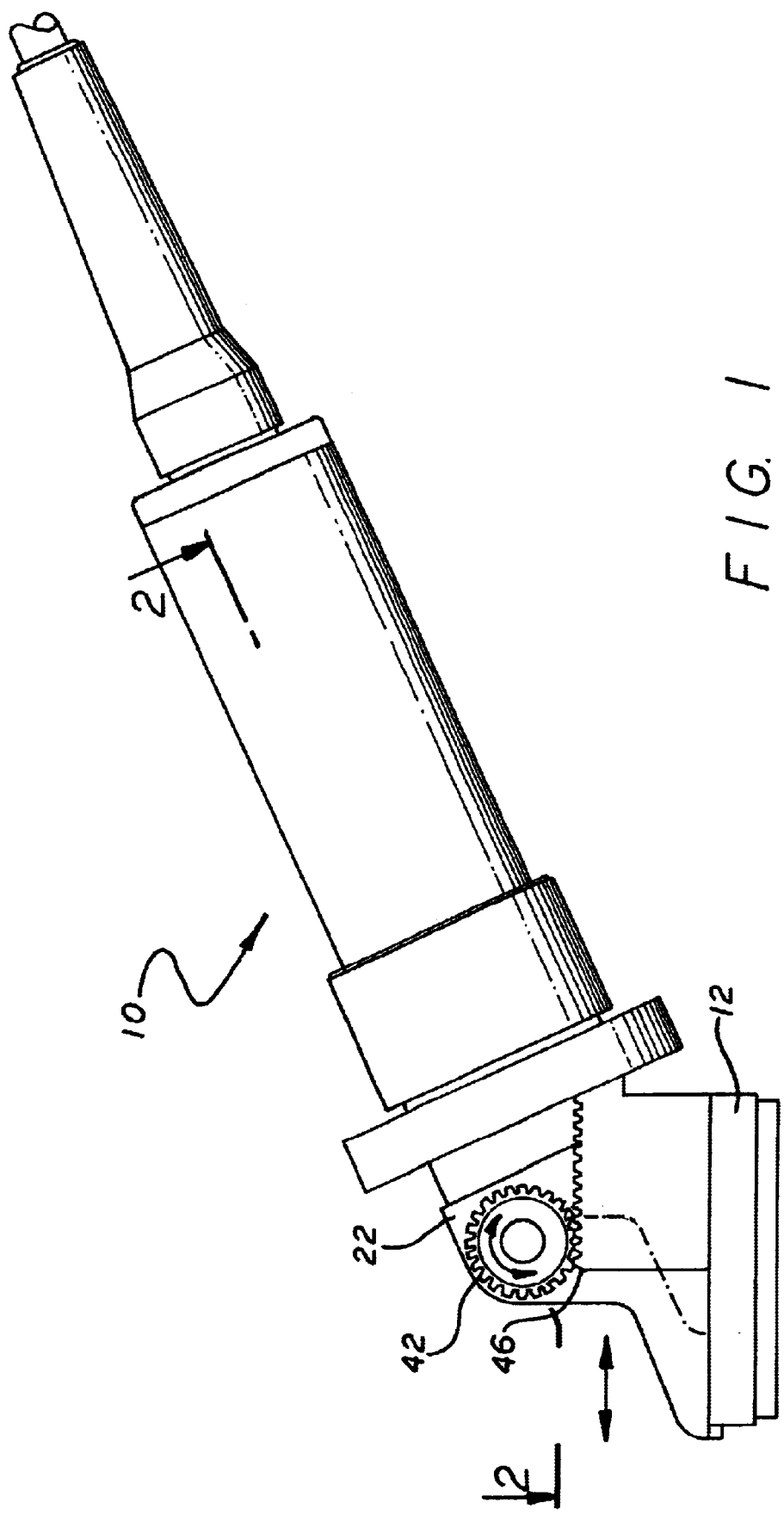
FIG. 1 is a side view of an embodiment of a medical device of the present invention.

Referring to the drawings more particularly by reference numbers, FIGS. 1–5 show an embodiment of a medical device 10 of the present invention. The device 10 may include a ring 12 that is placed onto a cornea (not shown). The ring 12 may have a port 14 which is coupled to a vacuum source (not shown). The vacuum source may create a vacuum pressure that pulls the ring 12 onto the cornea. The vacuum pressure prevents the ring 12 from moving during a procedure.

The device 10 may have a blade 16 that is located within an opening 18 of the ring 12. The blade 16 can move within the opening 18 in a first direction and a second transverse direction. The simultaneous movement of the blade 16 can create a cut across the surface of the eye. The device 10 may include a plate 19 that is mounted to the ring 12 and which flattens the cornea.

The blade 16 is attached to a blade holder 20. The blade holder 20 is attached to a head 22. The head 22 and blade holder 20 both move with the blade 16 relative to the ring 12. The blade holder 20 moves in the second direction while being pulled in the first direction. The head 22 only moves in the first direction.

Figure 2:
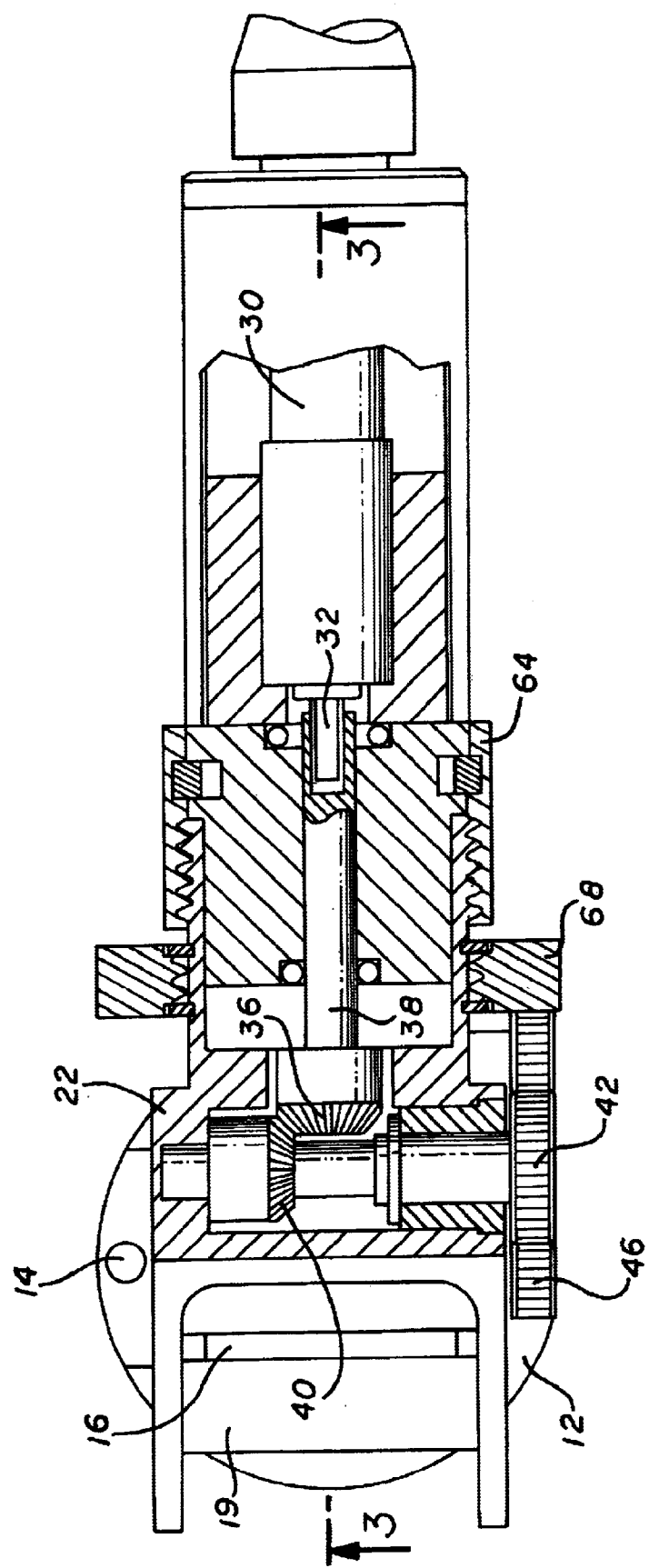
FIG. 2 is a cross-sectional view taken at line 2—2 of FIG. 1.
Figure 3:
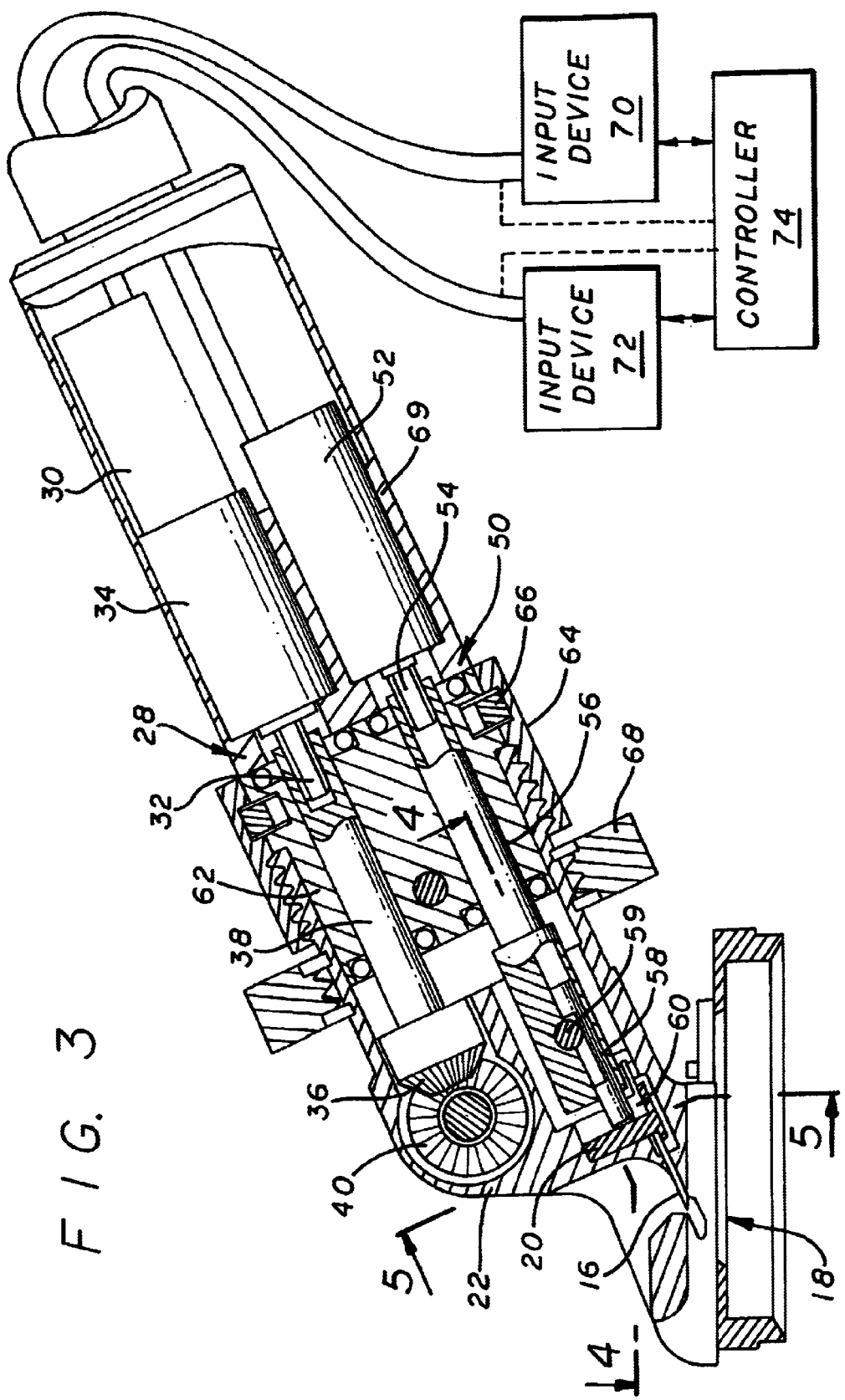
FIG. 3 is a cross-sectional view taken at line 3—3 of FIG. 2.

Referring to FIGS. 2 and 3, the device 10 includes a first drive mechanism 28 which moves the head 22, the blade holder 20 and the blade 16 in the first direction. The first drive mechanism 28 may include a first motor 30 that is coupled to an output shaft 32 by a gear reduction box 34. By way of example, the motor 30 may be an electric motor. The motor 30 may be coupled to a first gear 36 by a shaft 38 that is attached to the output shaft 32.

The first gear 36 may be coupled to a second gear 40 that is mounted to the head 22. The second gear 40 may be connected to a third gear 42 by a shaft 44. The third gear 42 may be coupled to a gear rack 46 (see also FIG. 1). The first 36 and second 40 gears may be of the bevel type so that rotation of the motor output shaft 32 imparts a corresponding rotation of shaft 44 and third gear 42. Rotation of the third gear 42 along the gear rack 46 causes the head 22, blade holder 20 and blade 16 to move in the first direction.

As shown in FIG. 1, the gear rack 46 may be located on a pedestal 48 that is attached to the ring 12. The pedestal 48 elevates the rack 46 above the cornea so that there is a low probability of an eyelash becoming stuck in the rack and pinion gear assembly.

Figure 4:
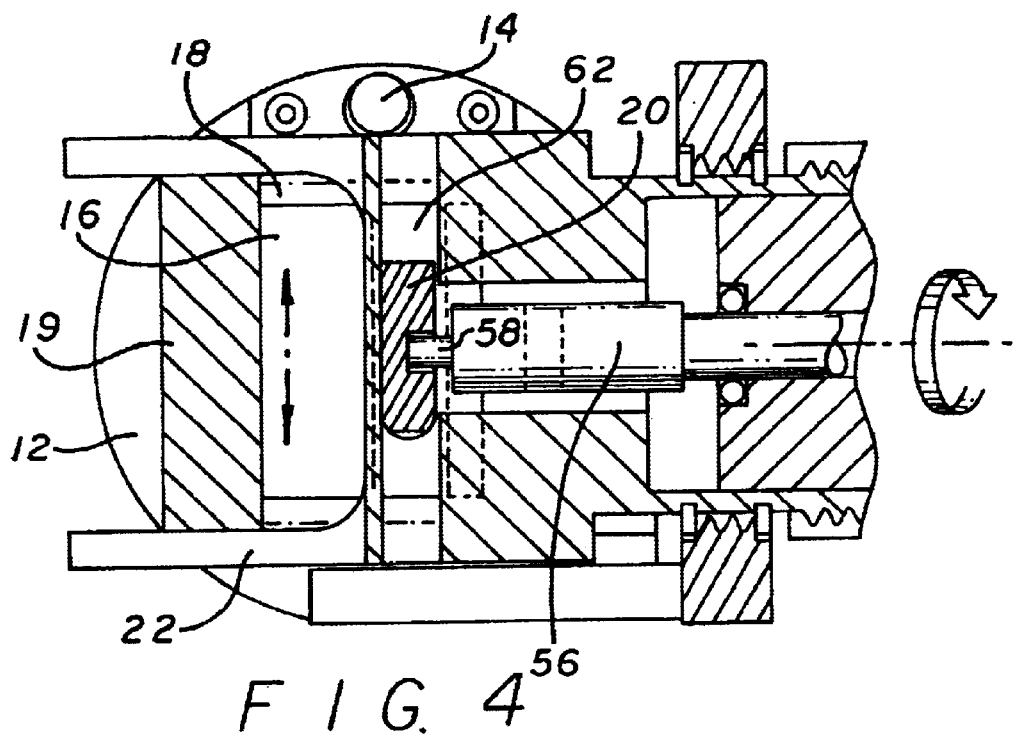
FIG. 4 is a cross-sectional view taken at line 4—4 of FIG. 3.
Figure 5:
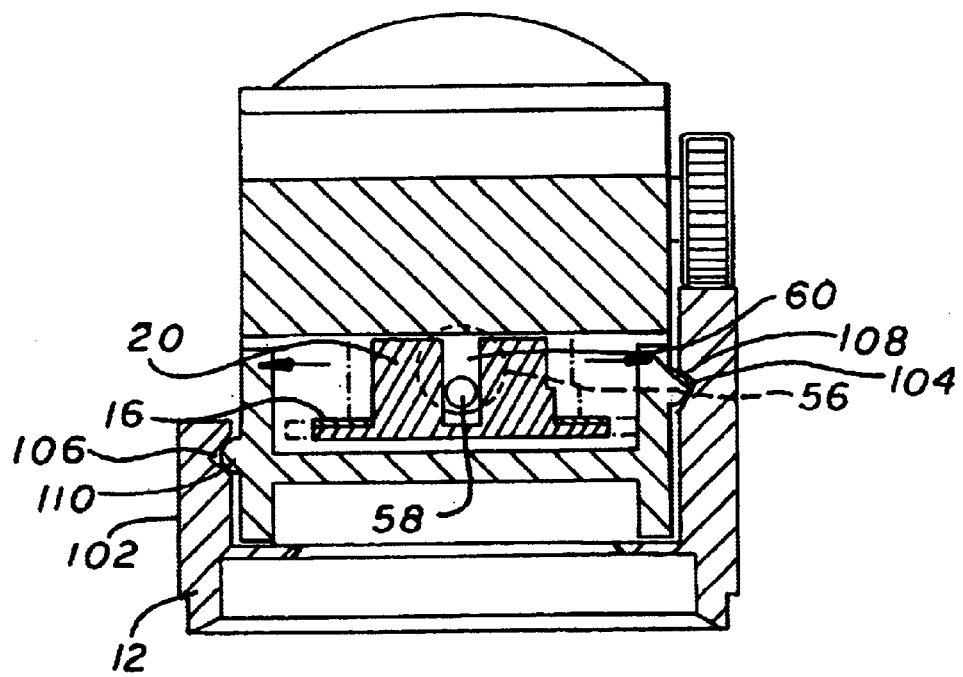
FIG. 5 is a cross-sectional view taken at line 5—5 of FIG. 3.

Referring to FIGS. 3–5, the device 10 may also have a second drive mechanism 50 that moves the blade holder 20 and the blade 16 in the second direction. The second drive mechanism 50 may include a second motor 52 which has an output shaft 54. By way of example, the motor 52 may be an electric motor. The output shaft 54 may be attached to a shaft 56 which has an eccentric cam pin 58. The cam pin 58 may be captured within the shaft 54 by another pin 59. The eccentric cam pin 58 fits within a slot 60 of the blade holder 20.

Rotation of the motor output shaft 54 moves the pin 58 about the center axis of the shaft 56. The eccentric rotation of the pin 58 moves the blade holder 20 and blade 22 within a slot 62 of the head 22 in the second direction. The pin 58 slides along the blade holder slot 60 in a vertical direction so that the blade 16 does not move into and out of the cornea.

The output shafts 38 and 56 may extend through a bulkhead 62 that is partially located within the head 22. A collar 64 and clip 66 attach the bulkhead 62 to the head 22. The device 10 may further have a lacking ring 68 for the collar 64. The motors 30 and 52 may be housed within a motor casing 69.

The first motor 30 may be connected to a first input device 70. The second motor 52 may be connected to a second input device 72. By way of example, the input devices 70 and 72 may be foot pedals which can be operated by a surgeon to control the actuation and speed of the motors 30 and 52. This allows the surgeon to separately control the movement of the blade 16 in the first direction and the movement of the blade 16 in the second direction. The surgeon can thus vary the shape and size of the cut.

The device 10 may further include a controller 74 which can be programmed to control the first 28 and second 50 drive mechanisms. The controller 74 can be used in conjunction with the input devices 70 and 72. The controller 74 may have programmable limit functions which limit the speed of the motors 30 and 52.

Figure 6:
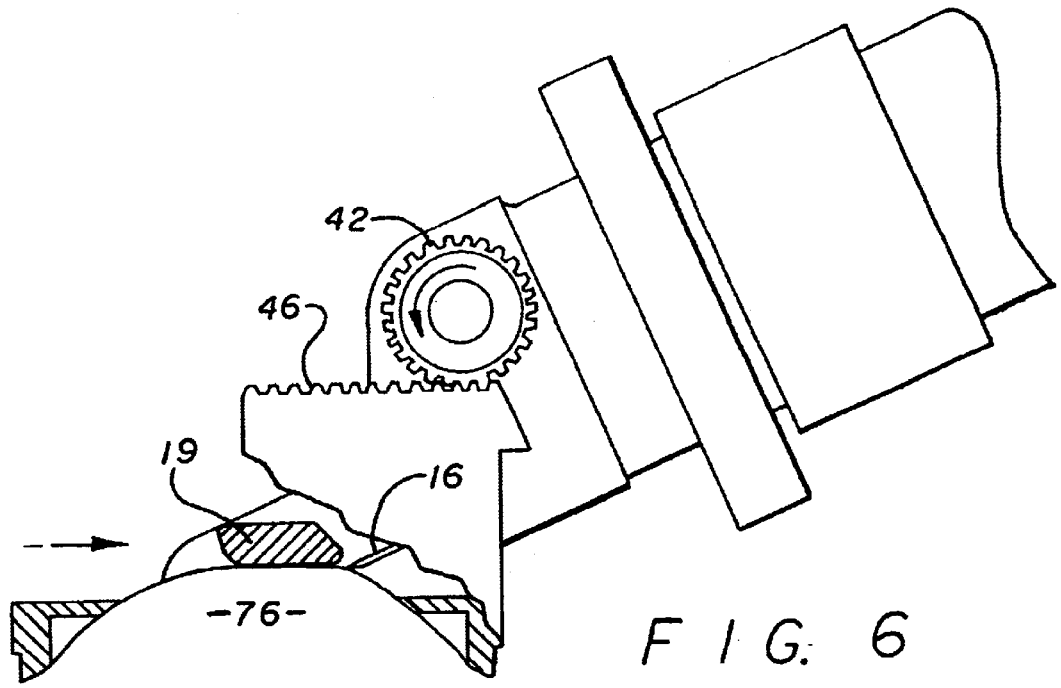
FIG. 6 is a side sectional view showing the device placed on a cornea.
Figure 7:
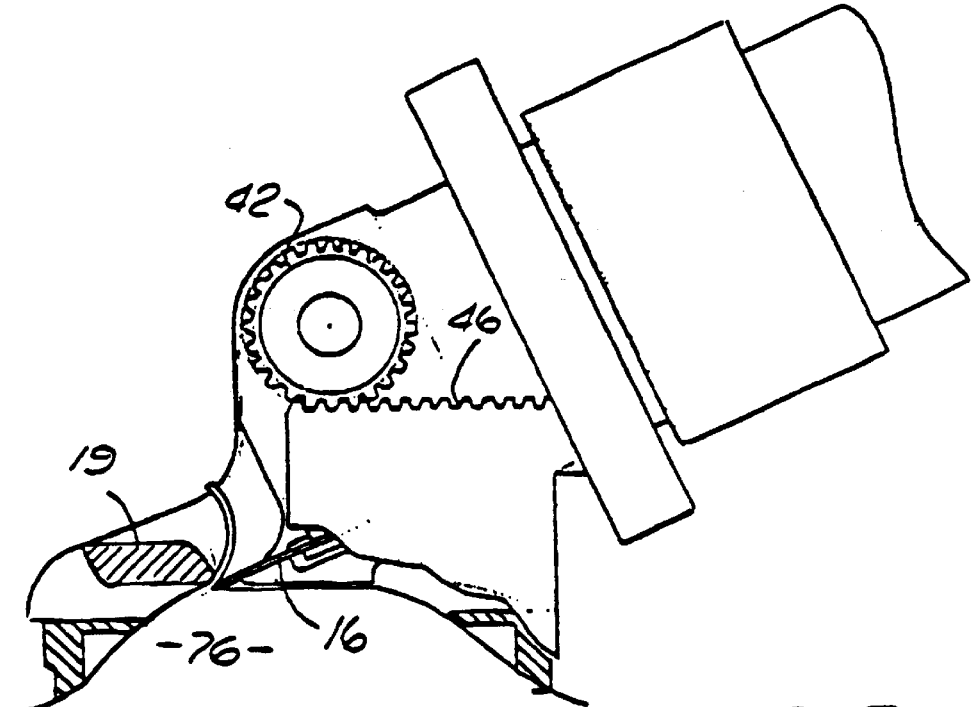
FIG. 7 is a side sectional view showing the device cutting the cornea.

As shown in FIGS. 6 and 7, in operation the ring 12 is placed on a cornea 76. The plate 19 tends to flatten the cornea 76 adjacent to the blade 16. The surgeon actuates the first 28 and second 50 drive mechanisms to move the blade 16 in the first and second directions. The movement of the blade cuts the cornea 76.

FIGS. 8 and 9 show linear bearings of the head 22 and the ring 12. The medical device 10 may utilize tongue and groove bearings to couple the head 22 to the ring 12. The tongue and groove linear bearings may be configured so that the head 22 can be inserted into the ring 12 from a vertical direction. This is to be distinguished from the dovetail arrangements used in the prior art where the head 22 must be inserted from a horizontal direction.

The ring 12 may have a first sidewall 100 and a second sidewall 102. The first sidewall 100 may include the gear rack 46 that is coupled to the third gear 42 shown in FIG. 1. Each sidewall 100 and 102 may have a generally V-shaped groove 104 and 106, respectively. The grooves 104 and 106 may extend along the entire length of each wall 100 and 102.

The head 22 may have a pair of tongues 108 and 110. Tongue 108 can be inserted into groove 104. Likewise, tongue 110 can be inserted into groove 106 so that the head 22 can slide across the ring 12. Each tongue 108 and 110 preferably has a radial outer surface. The radial surface of each tongue 108 and 110 creates contact at two points of each V-shaped groove 104 and 106. The two point contact aligns the tongues 108 and 110 within the grooves 104 and 106 and minimizes the friction between the head 22 and the ring 12.

Tongue 108 and groove 104 are located a distance d1 from a base surface 112. The tongue 110 and groove 106 are located a distance d2 from the base surface 112. The distance d1 may be greater than the distance d2 to provide a keying function for the assembly of the head 22 to the ring 12. The unequal distances insure that the head 22 is assembled onto the ring 12 so that the third gear 42 is mated with the gear rack 46.

Figure 10A:
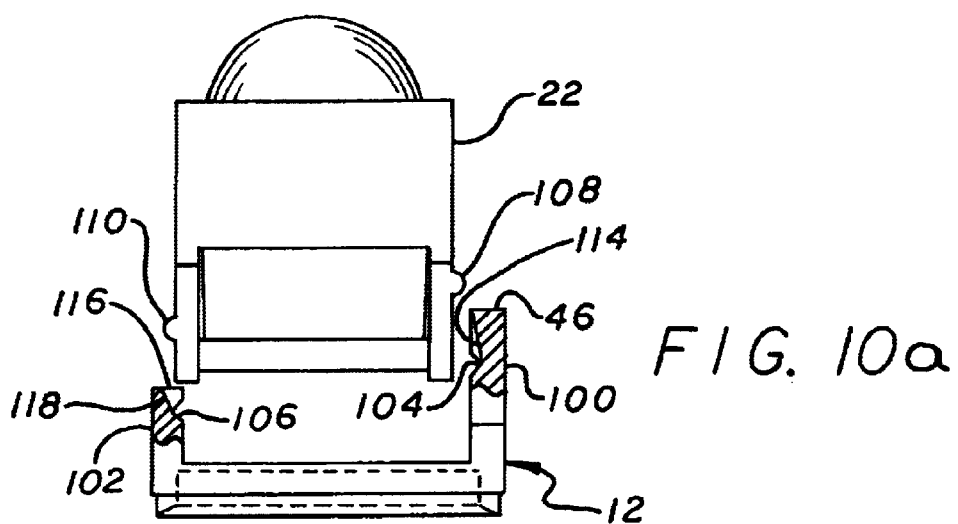
FIGS. 10a–c are side views showing the head being assembled to the ring taken at line 10—10 of FIG. 9.
Figure 10B:
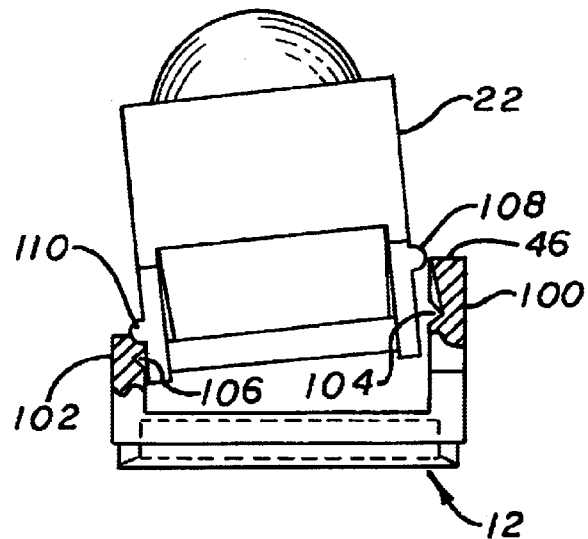
Figure 10C:
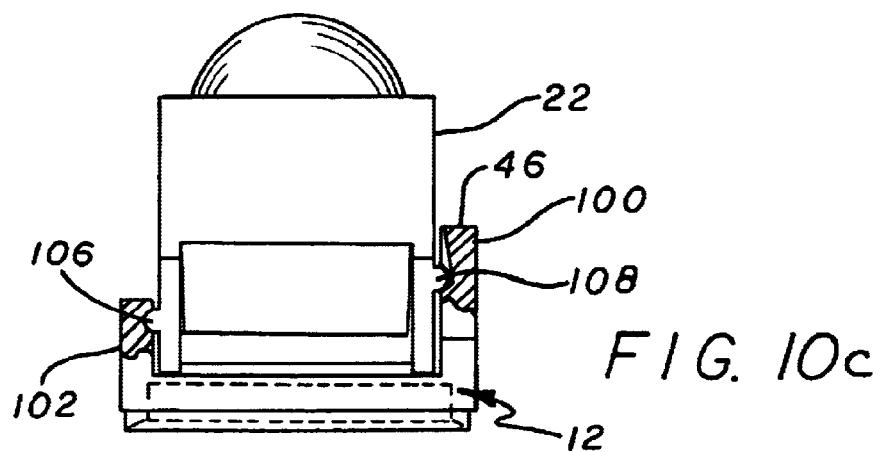
Figure 13:
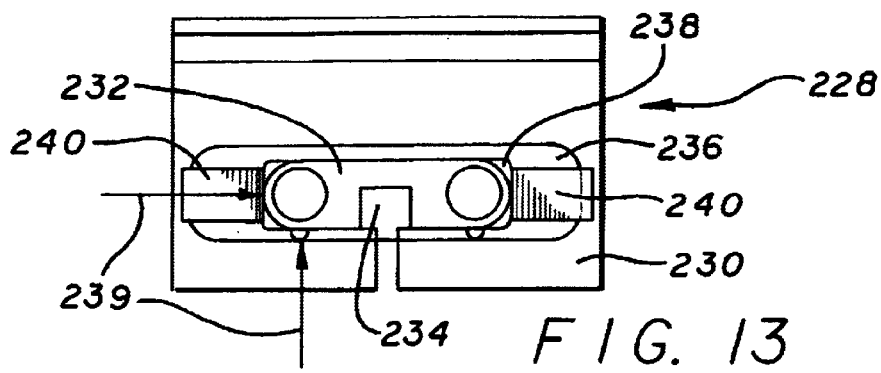
FIG. 13 is a top view of a blade holder assembly of the device.

FIGS. 10a–c show a method for assembling the head 22 to the ring 12. The head 22 is moved toward the ring 12 in a vertical direction as indicated by the arrow. A portion of the first sidewall 100 may have a chamfered surface 114 that tapers inwardly from the gear rack 46 to the groove 104 as shown in FIG. 8. Likewise, a portion of the second sidewall 102 may have a chamfered surface 116 that tapers outwardly from a top surface 118 to the groove 106. The inward taper of the chamfered surface 114 leaves sufficient area on the top surface of the first sidewall 100 for the gear rack 46.

A surgeon can push down on the head 22 so that the tongues 108 and 110 slide down the chamfered surfaces 114 and 118. The head 22 may be slightly tilted so that the tongue 108 clears the gear rack 46. The head 22 can be pushed until the tongues 108 and 110 snap into the grooves 104 and 106 to complete the assembly. The linear bearings of the present invention do not require an alignment of the tongues with the grooves and thus reduce the complexity of assembling the device.

The tongue and groove arrangement shown in FIGS. 8 and 9 may be implemented into a surgical device which has a single motor and a transmission that couples the gears to the single motor. By way of example, the motor and transmission may be the same or similar to the device shown and described in U.S. Pat. No. Re. 35,421 issued to Ruiz et al., which is hereby incorporated by reference.

FIG. 11 shows an alternate embodiment of a medical device 200. The device may include a head 202 that can move relative to a vacuum ring 204. The vacuum ring 204 may have a first sidewall 206 and a second sidewall 208. Each sidewall 206 and 208 may have a groove (not shown) that guides a corresponding linear bearing 209 of the head 202 in a manner that is the same, or similar, to the embodiment shown in FIGS. 10a–c. The device 200 may include a lead screw 210 that engages an inner thread (not shown) of the first sidewall 206. Rotation of the lead screw 210 will cause the head 202 to move across the ring 204.

As shown in FIG. 12, the lead screw 210 may be coupled to the output shaft 212 of a motor 214 by a belt 216 and a pair of pulleys 218 and 220. The device 200 may also have a pair of idler wheels 222 and 224 that create tension in the belt 216. It is desirable to provide a motor 214 that extends at an oblique angle relative to the ring 204. The oblique angle optimizes the ergonomics for a surgeon holding the device 200. The location of the idler wheels 222 and 224 compensates for the oblique angle between the motor 214 and the ring 204.

Rotation of the motor output shaft 212 will turn the pulley 220 and move the belt 216. Movement of the belt 216 will turn the pulley 218 and rotate the lead screw 210. Rotation of the lead screw 210 will move the head 202 across the ring 204. Using a belt 216 and lead screw 210 drive mechanism has a number of advantages over the spur gear, rack and pinion arrangements used in the prior art and shown in FIGS. 6 and 7. The belt 216 and lead screw 210 reduce wear and crowning. Additionally, the vibration energy may be transferred into the blade by the spur gears. The vibrating blade may create an undesirable cut of the cornea. The belt 216 may provide a damping element that can absorb vibration and prevent the transfer of energy into the blade.

The device 200 may include a motor 226 that can move a blade through an eccentric cam similar to the drive mechanism shown in FIGS. 4 and 5. FIGS. 13, 14, 15 and 16 show a blade holder assembly 228 that is located within the head 202. The assembly 228 may include a blade 230 that is captured by a blade holder 232. The blade holder 232 may have a groove 234 that cooperates with a rotating eccentric cam (not shown) to impart a translational movement of the blade 230.

Figure 14:
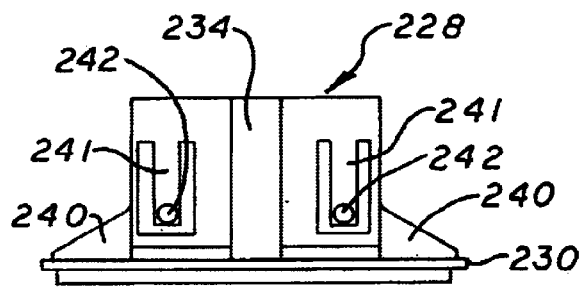
FIG. 14 is a front view of the blade holder assembly.
Figure 15:
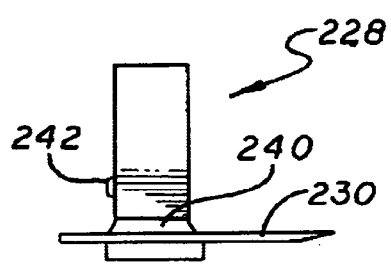
FIG. 15 is a side view of the blade holder assembly.
Figure 16:
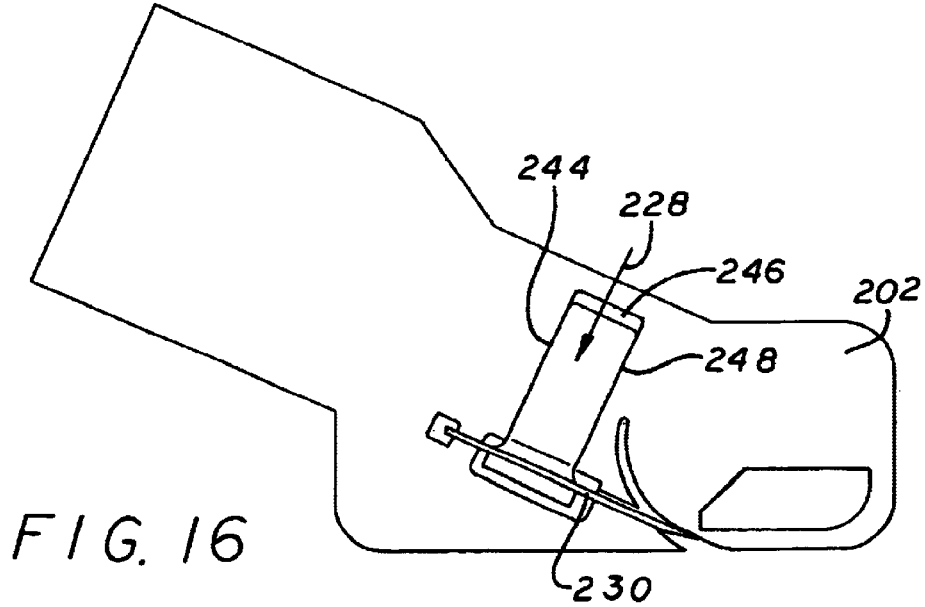
FIG. 16 is a side view showing the blade holder assembly within a head of the device.

The assembly 228 may include an insert 236 located within an opening 238 of the blade 230. The insert 236 may be constructed from a plastic material that deforms when the blade 230 is pushed onto the holder 232. The deformed insert 236 may function as a retention spring that exerts spring forces 239. The spring forces prevent the blade 230 from moving relative to the blade holder 230 during operation of the device 200. Additionally, the insert 236 may have a pair of retractable clips 240 that can retain the blade 230 in the z-axis. The clips 240 deflect inward when the blade 230 is pushed onto the blade holder 232 and deflect back out when the blade 230 is seated in the holder 232 as shown in FIGS. 14 and 15.

The insert 236 may also have a pair of spring levers 240. Each lever 241 may have a protrusion 242 that can function as a bias spring to exert a spring force on a wall 244 of the head 202 when the assembly 228 is placed within the head cavity 246. The spring force created by the protrusions 242 will push the assembly 228 into a wall 248 of the head 202. The wall 248 may be a datum zero reference surface. Pressing the assembly 228 against a datum zero wall reduces the tolerance build-up of the assembly.

FIG. 17 discloses a blade loader 250 that can be used to load the assembly 228 into the head cavity. The loader 250 may include a body 252 with an inner cavity 254 that receives the assembly 228. The body 252 may also have one or more openings 256 that are adapted to receive alignment pins 258 of the head 202. The pins 258 and openings 256 align the inner cavity 254 of the loader 250 with the head 202 so that the assembly 228 is accurately loaded into the head cavity.

The assembly 228 can be pushed into the head cavity 246 with a plunger 260. The plunger 260 can be manually actuated. Alternatively, the plunger 260 may be automatically actuated by a solenoid or other means. The plunger 260 may have a stop 262 that can engage a surface 264 of the body 252 to limit the movement of the assembly 228 into the head cavity 246. The stop 262 can assist in centering the assembly 228 so that the eccentric cam can be inserted into the corresponding groove of the blade holder.

FIGS. 18 and 19 show an embodiment of the ring 202. The ring 202 may have a tube port 270 that can receive a vacuum tube 272. The vacuum tube 272 can be coupled to a source of vacuum (not shown). The device 200 may include a ring insert 274 that is pressed into the ring 202. The ring insert 274 may be constructed from a plastic material that deforms when inserted into the ring 202.

The ring insert 274 may have a recessed outer rim 276 that cooperates with the ring 202 to form an annular ring channel 278. The channel 278 is in fluid communication with the vacuum tube 272 and a plurality of vacuum ring openings 280, wherein air flows through the openings 280 and into the tube 272. The openings 280 are placed adjacent to the cornea. The air flow through the openings 280 creates a vacuum pressure that secures the ring 202 to the cornea.

Each opening 280 preferably has a length that is greater than a width. This configuration provides an opening area sufficiently large enough to minimize pressure drops, while creating an aspect ratio that inhibits tissue occlusions within the openings 280. The slit configuration of the openings 280 shown in FIG. 19 is less likely to occlude than a circular opening found in rings of the prior art.

FIG. 20 shows an alternate embodiment of a ring insert 274'. The ring 274' may have an oblong shaped inner opening 282. The oblong shape creates additional space to compensate for the hinge 284 of the corneal flap 286. This allows the flap 286 to be longer and provides additional corneal area that can be ablated in a LASIK procedure.

FIG. 21 shows a stop mechanism 290 of the device 200. The stop mechanism 290 may include a stop pin 292 that extends from the head 202. The stop pin 292 may engage a stop surface 294 of the second sidewall 208. The stop mechanism 290 limits the length of the flap created in the cornea. The distance that the stop pin 292 extends from the head 202 can be adjusted to vary the length of the flap. The stop surface 294 is located above the top surface 296 of the ring 202. Elevating the stop surface 294 reduces the likelihood that an eye lash or other object may extend up into the stop mechanism 290 to impede the stop pin 292 and prematurely stop the movement of the blade.

Figure 22A:
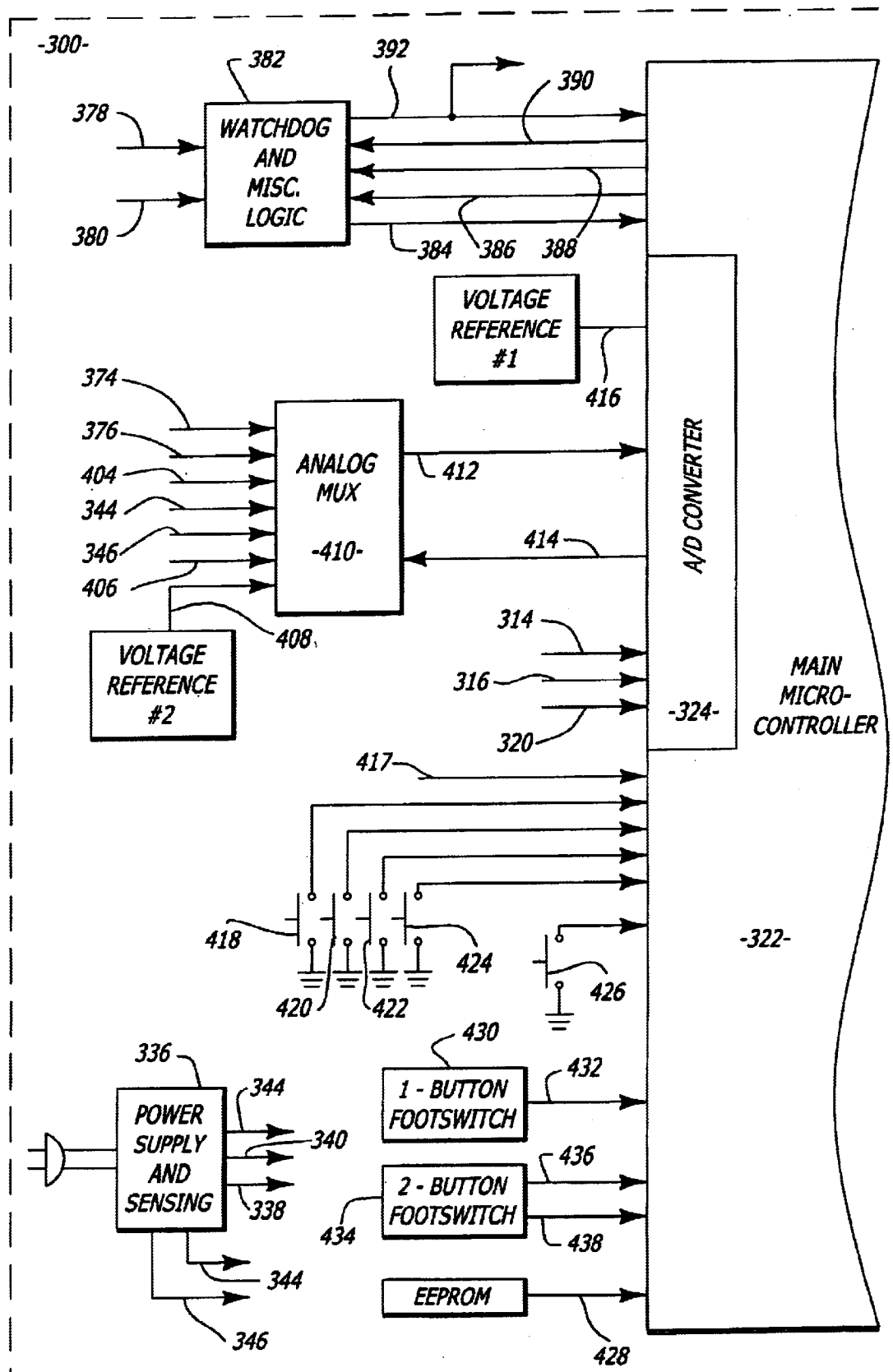
FIGS. 22a and 22b are a schematic of a console for the device.
Figure 22B:
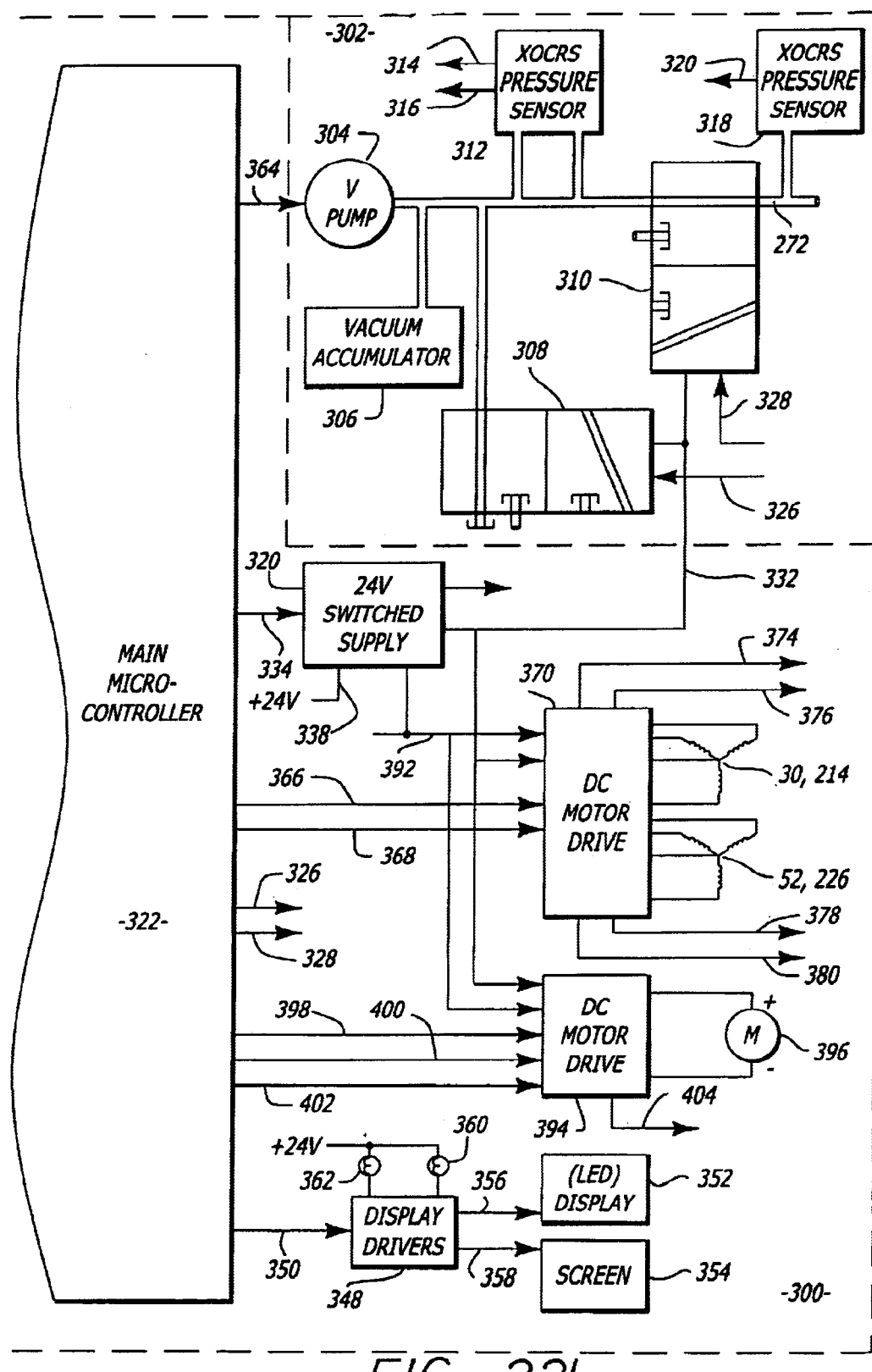

FIGS. 22a and 22b show a console 300 that can operate a medical device. For example, the console 300 can operate either device 10 or device 200. The console 300 may be coupled to a vacuum system 302. The vacuum system 302 may include the vacuum tube 272 that is coupled to the vacuum ring (not shown). The system 302 may include a vacuum pump 304 that creates a vacuum pressure in the tube 272 and an accumulator 306 that provides a relatively constant vacuum pressure within the system.

The vacuum system 302 may include a solenoid actuated pressure relief valve 308 that can be switched between an open position and a closed position. In the open position the valve 308 couples the tube 272 to atmosphere to release the vacuum pressure in the system 302. The vacuum system 302 may also have a solenoid actuated on-off valve 310 that can be switched between an open position and a closed position. In the open position the valve 310 allows air to flow through the tube 272. In the closed position the valve 310 prevents air from flowing through the tube 272.

The vacuum system 302 may have a first pressure sensor 312 that is in fluid communication with the tube 272. The first sensor 312 provides analog output signals on lines 314 and 316 that correspond to the vacuum pressure within the tube 272. The system 302 may also have a second pressure sensor 318 that can sense the vacuum pressure upstream from the on-off switch 310. The second sensor 318 provides an analog output signal on line 320.

The console 300 may include a micro-controller 322 that can process data and instructions in accordance with a firmware and/or hardware routine(s). The controller 322 may have an on-board analog to digital (A/D) converter 324 that is connected to the pressure sensor lines 314, 316 and 320. The A/D converter 324 converts the analog output signals from the sensors 312 and 318 to digital bit strings that can be processed by the controller 322.

The controller 322 can provide output signals on lines 326 and 328 to switch the valves 308 and 310, respectively. The console 300 may include a power supply switch 330 that provides power to the valves 308 and 310 through line 332. The controller 322 may switch the power switch 330 with an output signal on line 334. The switch 330 may receive power from a power supply 336 through power bus 338. The power supply 336 may also provide different power levels on output busses 340 and 342. By way of example, power bus 338 may have a voltage potential of 24 volts, power bus 340 may have a voltage of 12 volts and bus 342 may be at 5 volts. The power supply 336 may also provide sensing output signals on lines 344 and 346.

The controller 322 may be connected to display drivers 348 by line(s) 350. The drivers 348 can be connected to a 7-segment light emitting diode (LED) display 352 and/or a screen 354 by lines 356 and 358, respectively. The LED 352 and/or screen 354 can display various alphanumeric characters such as the vacuum pressure within the tube 272. The drivers 348 may also be connected to a first indicator light 360 and a second indicator light 362. By way of example, the first indicator light 360 may be illuminated when there has been a reduction of vacuum that exceeds a predetermined value. The second indicator light 362 may be illuminated when vacuum is provided to the device 200. The indicator light 362 may be illuminated when the controller 322 enables the pump 304 through line 364 and switches the valve 310 to the open position through line 328.

The controller 322 can operate the system in accordance with a pressure sensing routing. In this routine the controller 322 reads the output signals of the pressure transducers 314 and 318 and may provide a numeric indicator of the pressure on the LED 352 and/or screen 354. The controller 322 can also compare the pressure values with threshold value(s). If the vacuum pressure within the tube 272 exceeds a threshold value then the controller 322 may provide a message to this effect on the screen 354. The console 300 may also emit an audio signal to alert the surgeon.

The controller 322 can also provide a diagnostic routine to determine the cause of the vacuum loss. The controller 322 can switch the on-off valve 310 to the off position and then read the pressure from sensors 312 and 318. If the pressure from sensor 318 is lower than sensor 312 this may provide an indication that there is a fluid leak at the ring. The screen 354 may display a message such as RING LEAK. The controller 322 may also compute a time rate of change of pressure from sensor 318. The pressure reading from sensor 312 may provide an indication that the pump 304 is malfunctioning. The sensor 312 may also provide an indication that the vacuum pump is not properly functioning even though the tube appears to have an adequate vacuum pressure because of an occlusion in the ring opening(s). It is imperative that the vacuum system always have a vacuum pressure sufficient to maintain the position of the ring during the cutting procedure.

The controller 322 may provide output signals on lines 366 and 368 to control device motors 30, 214 and 52, 226. The signals may be provided to a 3-phase brushless DC motor driver 370 that can control the speed of the motors 30, 214 and 52, 226. The voltage levels of the motors can be fed back to the controller 322 on lines 374 and 376. The driver 370 can determine the actual motor speed by sensing the back emf of the motor or other means. The speed of each motor 30, 214 and 52, 226 can be provided on lines 378 and 380, respectively. The controller 322 may utilize the actual speed of each motor to provide a closed feedback control of the motors.

The speed signals may be provided to the controller 322 through a safety "watchdog" circuit 382. The circuit 382 may relay the signals to the controller 322 on line 384. The safety circuit 382 may receive input signals from the controller 322 on lines 386, 388 and 390. The circuit 382 may also generate a watchdog signal on line 392. The watchdog signal 392 may be provided to the driver 370 to turn off the motors and the power switch 330 to release the vacuum in the tube 272. The relief valve 308 may be normally open so that the termination of power will open the valve 308. The on-off valve 310 may be normally closed so that a termination of power closes the valve 310.

The console 300 may also have a brushed DC motor driver 394 that is connected to a single motor 396 that moves the blade in both directions. The driver 394 may receive input signals from the controller 322 on lines 398, 400 and 402. The speed of the motor 396 can be provided on line 404. The inclusion of the driver 394 makes the console compatible with different types of devices including devices with either a single motor or two motors.

Control lines 344, 346, 374, 376, 404, 406 and 408 can be coupled to the A/D converter 324 through an analog multiplexor 410. Control line 406 can provide a feedback signal from the power switch 330. The output of the multiplexor 410 can be provided to the A/D converter 324 on line 412. The multiplexor can be selected through line(s) 414. The multiplexor allows additional inputs to be provided to a conventional 8 pin A/D converter 324. The A/D converter 324 may receive a reference voltage on line 416. The reference voltages can be compared to determine safety characteristics of the console.

Control line 417 is connected to a knob that can be rotated by a user. Rotation of the knob varies the voltage to the controller 322. The voltage can be associated with a variable parameter depending upon the state of switches 418, 420, 422 and 424. If none of the switches 418, 420, 422 or 424 are closed then the voltage of line 417 is associated with a maximum pre-set vacuum pressure. The controller 322 will control the vacuum system 302 so that the vacuum pressure does not exceed the maximum pre-set value. The maximum vacuum pressure can be adjusted by rotating the knob.

By closing switch 418 the user can adjust the volume of an audible tone created to warn the surgeon of an inadequate vacuum pressure. By closing switch 420 the user can adjust the speed of motor 30, 214 and thus the tracking speed of the blade. Closing switch 422 allows the user to adjust the speed of motor 52, 226 and the cutting speed of the blade. The user can adjust the amount of vacuum loss that is acceptable before the indicator is activated by closing switch 424. This parameter may be used to set the threshold value for the indicator 360. The values associated with motor speed, etc. may be stored in a non-volatile memory device such as an EEPROM 428. The switches may be located at the rear panel of the console so that someone does not inadvertently change the settings.

The console 300 may have another switch 426 that can be closed to initiate the vacuum system. When this switch 426 is closed, the pump 304 is enabled, the relief valve 308 is closed and the on-off valve 310 is opened. The vacuum system 302 may also be activated by depressing a button of a foot pedal 430 that is connected to console by line 432.

The controller 322 may also be connected to a second foot pedal 434 by lines 436 and 438. The foot pedal 434 may have a pair of buttons. One button can be depressed to activate the motors and cause the head to move in a "forward" direction. The other button can be depressed to move the head in a "backward" direction.

In operation, the surgeon can place the ring on the cornea and then initiate the vacuum system 302 by closing switch 426 or actuating the foot pedal 430. The surgeon can then activate the motors 30, 214 and 52, 226 by actuating the foot pedal 434. The controller 322 can control the motor speed through the closed feedback loop. The controller 322 can also monitor the pressure of the vacuum system 302 and provide an indication of both the vacuum pressure and when the pressure exceeds a threshold value. The console of the present invention thus provides information to the surgeon regarding the pressure of the vacuum system.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A medical device for cuffing a cornea, the medical device being coupled to a source of vacuum, comprising:

a ring that has a bottom surface that comes into contact with the cornea and an opening that is in fluid communication with the source of vacuum, said opening having a slitted profile that extends along said bottom surface with a length dimension that is greater than a width dimension;

a head that can move relative to said ring;

a blade the is coupled to said head; and, a motor that is coupled to said head to move said head relative to said ring.

2. The medical device of claim 1, wherein said ring has a center opening that has an oblong shape.

3. A medical device for cutting a cornea, the medical device being coupled to a source of vacuum, comprising:

a ring that has a bottom surface that comes into contact with the cornea and a slitted vacuum opening having a slitted profile that extends along said bottom surface;

a head that can move relative to said ring;

a blade that is coupled to said head; and, a motor that is coupled to said head to move said head relative to said ring.

4. The medical device of claim 3, wherein said ring has a center opening that has an oblong shape.

5. The medical device of claim 4, wherein said ring has a center opening that has an oblong shape.

6. The medical device of claim 4, wherein said opening means includes a slitted opening in said ring.

7. A medical device for cutting a cornea, the medical device being coupled to a source of vacuum, comprising:

a ring that has a bottom surface that comes into contact with the cornea and contains opening a slitted means that extends along said bottom surface for allowing a vacuuming pressure to maintain said ring onto the cornea;

a head that can move relative to said ring;

a blade that is coupled to said head; and, a motor that is coupled to said head to move said head relative to said ring.

8. A method for attaching a medical device to a cornea, comprising:

placing a bottom surface of a ring onto the cornea, the ring having a slitted opening with a slitted profile that extends along the bottom surface; and, creating a vacuum pressure through the slitted opening in the ring.

* * * * *